United States Patent [19]

Halstrom et al.

[11] 4,267,344
[45] May 12, 1981

[54] N-SUBSTITUTED N-CARBOXYANHYDRIDES OF α-AMINO ACIDS AND THEIR APPLICATION IN THE PREPARATION OF PEPTIDES

[75] Inventors: John B. Halstrøm, Lyngby; Károly G. Kovács, Farum, both of Denmark

[73] Assignee: Proteinkemisk Institut. tilknyttet Akademiet for de tekniske Videnskaber, Copenhagen, Denmark

[21] Appl. No.: 961,944

[22] Filed: Nov. 20, 1978

Related U.S. Application Data

[63] Continuation-in-part of Ser. No. 857,575, Dec. 5, 1977, abandoned, which is a continuation of Ser. No. 576,430, May 12, 1975, abandoned, which is a continuation of Ser. No. 398,805, Sep. 19, 1973, abandoned.

[30] Foreign Application Priority Data

Sep. 22, 1972 [DK] Denmark ............................. 4702/72

[51] Int. Cl.³ .............................. 549 26; C07D 407/02; C07D 412/02; C07D 421/02
[52] U.S. Cl. ...................................... 548/227; 260/6; 260/8; 260/112.5 R; 260/239 R; 260/335; 549/27; 560/110; 562/439; 568/442
[58] Field of Search ................... 260/335, 328, 307 D, 260/239 R; 560/39; 562/444, 553; 549/26, 27; 548/227

[56] References Cited

U.S. PATENT DOCUMENTS 3,671,239   6/1972   Zweig ............................. 260/307 B

FOREIGN PATENT DOCUMENTS 1518289   5/1969   Fed. Rep. of Germany ............. 560/39
41-21337  12/1966  Japan ......................................... 560/39
646033   11/1950   United Kingdom ................. 260/307 B

OTHER PUBLICATIONS

Velluz et al., Chemical Abstracts, vol. 49, cols. 9534–9535 (1955) (abst. of Bull. Soc. Chim. 1954, 1012–1015).
Shimonishi et al., Bull. Chem. Soc. Japan, vol. 35, pp. 1966 to 1970 (1962).

Primary Examiner—John D. Randolph
Attorney, Agent, or Firm—Hubbell, Cohen, Stiefel & Gross

[57] ABSTRACT

N-Substituted N-carboxyanhydrides of α-amino acids, useful in peptide syntheses, and peptide synthesis process using such compounds, are disclosed. The N-substituent is penta(lower alkoxy)benzyl, or optionally substituted 9-xanthyl, 9-thioxanthyl or 9-selenoxanthyl.

5 Claims, No Drawings

N-SUBSTITUTED N-CARBOXYANHYDRIDES OF α-AMINO ACIDS AND THEIR APPLICATION IN THE PREPARATION OF PEPTIDES

CROSS-REFERENCE TO RELATED APPLICATIONS

This application is a continuation-in-part of co-pending application Ser. No. 857,575, filed Dec. 5, 1977, now abandoned, which is in turn a continuation of application Ser. No. 576,430, filed May 12, 1975, now abandoned, which is in turn a continuation of appln. Ser. No. 398,805, filed Sept. 19, 1973, now abandoned; the contents of said applications being incorporated herein by reference.

BACKGROUND OF THE INVENTION

1. Field of the Invention

The present invention concerns a novel class of N-substituted N-carboxyanhydride derivatives of α-amino acids. The compounds of the invention are valuable intermediates or reagents for use in peptide syntheses. The invention also relates to peptide syntheses process using the novel compounds.

2. Prior Art

The synthesis of peptides involves the establishment of amide bonds by the condensation of the carboxyl group of one amino acid with the amino group of another. In order to achieve the desired sequence and to avoid polycondensation, it is necessary to protect the functional groups which are not intended to react, i.e. the amino group of the carboxyl component and the carboxyl group of the amino component, respectively, as well as possible side-chain functional groups. All protecting groups must be sufficiently labile to allow quantitative removal without concomitant cleavage of peptide bonds or any other kind of destruction.

Shortly before the turn of the century, the first attempts at a stepwise assembly of amino acids into peptides were made. The lack of a selectively removable amino protecting group, however, imposed severe limitations upon the results which could be obtained at that time. This difficulty was not overcome until 1932, when the benzyloxycarbonyl group, which can be removed selectively by catalytic hydrogenation, was introduced.

In the decades where were to follow, a great number of smaller peptides were synthesized, and from 1950 to 1960, the first entirely synthetic peptide hormones, chemically and biologically identical with the natural ones, were produced.

The very principle of the synthesis remained practically unchanged throughout this period, but several improvements were introduced into the classical synthesis, such as more suitable types of derivatives and more varied ways of condensation; especially worthy of mention is the now most widely used method, employing tert.butoxycarbonyl for amino protection and N,N'-dicyclohexylcarbodiimide as activating reagent fr condensing agent.

In the classical peptide synthesis, the reaction proceeds in solution, where equivalent quantities of amino and carboxyl components are reacted, influenced by the activating reagent, e.g. N,N'-dicyclohexylcarbodiimide. At the end of the reaction, the product is isolated by precipitation, but due to co-precipitation of starting material and side-products, a time-consuming purification must usually be carried out. Thus, in the case of longer-chain peptides, recrystallization or re-precipitation is mostly insufficient, and one has to take recourse to counter-current distribution, gel-filtration or ion-exchange chromatography. This procedure is frequently very tedious, and yields of from 40% to 60% of the theoretical in fragment condensation, and from 60% to 90% in stepwise chain elongation are usually regarded as satisfactory.

In 1962, a novel concept, eliminating all solubility problems by rendering the growing peptide chain insoluble by covalent bonding to a resin matrix, was introduced (the so-called solid-phase peptide synthesis). Here, the washing-out of excess amino acid derivative and by-products can be carried out quantitatively with adequate volumes of various solvents without less of any of the resin-bound peptide. Moreover, the resin-bound peptide can be isolated simply by filtration, a fact which makes the process amenable to automation.

The principle of the solid-phase peptide synthesis is exemplified below in schematic form, t-BOC representing the tert.butoxycarbonyl group.

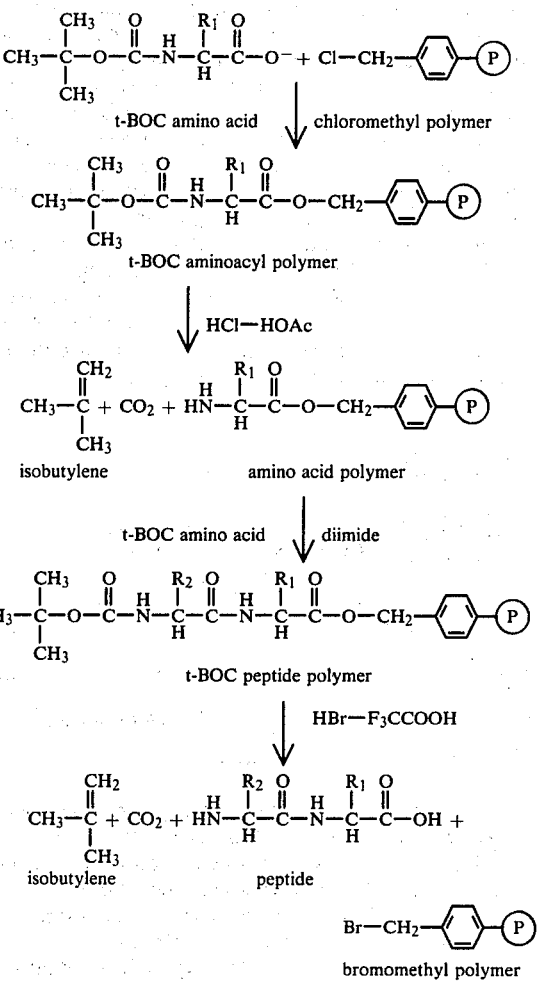

In the solid-phase synthesis, the growing peptide chain is constantly anchored by ist C-terminus to a resin, usually co-valently bound in the form of a benzyl ester to an insoluble styrene-divinylbenzene co-polymer. In each cycle of the synthesis, dissolved amino acid derivative is added, followed by the condensing agent, usually N,N'-dicyclohexylcarbodiimide. Notwithstanding the two-phase nature of the reaction, it proceeds quickly, due to efficient mixing and the pronounced swelling of the resin in the solvent used. Traditionally, the α-amino group of the amino acid is protected by the tert.butoxycarbonyl group, which, unlike the benzyloxycarbonyl group, is readily split off upon brief exposure to N hydrogen chloride in glacial acetic acid or dioxane after formation of the amide bond. When the peptide has attained the desired chain-length, the bonds to the resin and to the N-terminal and side-chain protecting groups are cleaved by briefly passing dry hydrogen bromide gas through a suspension of the peptide-resin in anhydrous trifluoroacetic acid. The liberated peptide is dissolved, and can be isolated as the hydrobromide. The removal of certain side-chain protecting groups does, however, require further treatment, which will not be dealt with here.

Recently, other methods of peptide synthesis have been developed, in which the growing peptide chain is anchored to a soluble resin; in principle, these syntheses offer the same technical advantages as the solid-phase synthesis, the actual method of effecting the separation being different, e.g. gel-filtration. In the following text, peptide syntheses of this kind and solid-phase syntheses will be referred to collectively as syntheses using polymeric carriers, or briefly, resin carrier syntheses.

Due to the danger of formation of peptides containing a wrong sequence because of incomplete reaction in certain steps of the resin carrier synthesis, a suitable excess of amino acid derivative is used, in general from two to three times the theoretical quantity, in order to make each step proceed to completion.

Certain activated amino acid derivatives are particularly prone to suffer rearrangement into inactive products. In consequence, the remaining quantity of derivative may be inadequate to ensure a quantitative reaction. A generally occurring rearrangement in carbodiimide syntheses is illustrated schematically below:

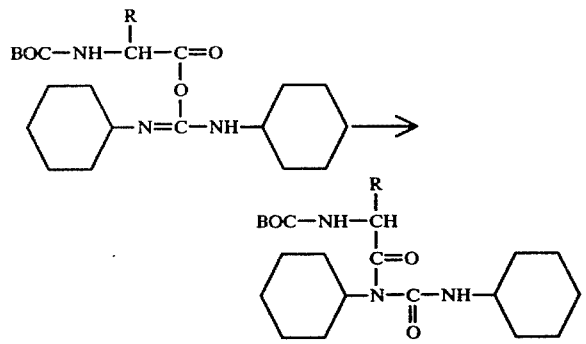

This rearrangement is especially pronounced in the case of glycine, and for this reason an excess of this amino acid is usually employed, in resin carrier syntheses generally five times the theoretical amount.

A further, marked disadvantage attending the use of activating reagents like e.g. dicyclohexylcarbodiimide is their high degree of reactivity, which requires an extensive protection of side chain functional groups, often a complete or so-called "global" protection. Furthermore, the interaction of the activating reagent and the N-protected amino acid produces an activated complex, the excess of which may well be isolated after the condensation, but cannot be utilized to regenerate the N-protected amino acid. In practice, therefore, this means that the excess of N-protected amino acid—a most expensive reagent—employed in each condensation step is lost. Even in classical syntheses in solution this is a serious drawback, because, due to the above-mentioned rearrangement, an excess of the N-protected derivative must often be used. In resin carrier syntheses this drawback assumes an even greater significance, since in order to achieve the very essential acceleration of the synthetic procedure, one has to acquiesce in the sacrifice of the large excess of N-protected amino acid, which especially in industrial-scale syntheses represents a great financial loss.

For this reason, there is a great current interest in finding other types of reagents and condensation methods which are not connected with disadvantages of the nature mentioned above. One solution suggested in this connection is the use of activated esters of amino acids, since the employment of such activated esters is not dependent upon the presence of added condensing agent, and consequently, no undesired conversion of the excess reagent takes place. Activated esters, among which especially p-nitrophenyl-, pentachlorophenyl-, and N-hydroxysuccinimide esters have found practical application, are, however, very reactive species, and particularly in the case of p-nitrophenyl and pentachlorophenyl esters, difficulties have been experienced in their preparation and storage. Moreover, such activated esters have often been found to react sluggishly in resin carrier syntheses.

A particularly interesting type of N-protected, reactive derivatives of α-amino acids for use in peptide syntheses are the so-called N-carboxyanhydrides of α-amino acids (amino acid NCAs), most of which can be prepared by the action of phosgene upon α-amino acids, and which are represented by the formula

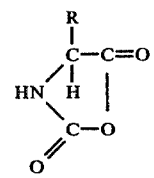

where R designates the side-chain of the amino acid. In these N-carboxyanhydrides, the anhydride moiety has a double rôle, namely that of activating the carboxyl function as well as protecting the amino function. In syntheses employing N-carboxyanhydrides, no additional condensing agent is used, whereby side-reactions with unprotected amino acid side-chains, occasioned by the presence of such agents, are avoided. Thus it has been reported that only the side-chain functions of lysine and cysteine need be protected. At the same time, a conversion of the added amino acid derivative into an activated form, which precludes the recovery of the derivative, is avoided.

The fact that the N-carboxyanhydride method, in spite of the abovementioned advantages, has not gained any widespread application, is due to a number of factors. One disadvantage of the N-carboxyanhydrides is their relative instability during storage; if a ring-opening occurs in just a small fraction of the N-carboxyanhydride molecules, the free amino groups formed will react with the activated carboxyl groups of other N-carboxyanhydride molecules, resulting in a steadily increasing polymerization by chain reaction, noticeable e.g. by a steady increase in the melting point. Under unfavourable storage conditions, this reaction may be complete in just a few days. Furthermore, for the same reason, special protective measures must be taken during the handling of N-carboxyanhydrides due to their reactivity, such as the exclusion of humidity by the use of e.g. a glove-box. Moreover, in model experiments N-carboxyanhydrides have been shown to react with the "wrong" side of the anhydride, i.e. with the carbonyl group attached to the nitrogen atom, so that by the reaction with the amino group of the amino component a carbonyl group is inserted between the two nitrogen atoms, forming an ureido acid. The more basic the amino component, the more extensive the formation of ureido acid. In resin carrier synthesis, where a large excess of acylating amino acid derivative is used, conventional N-carboxyanhydrides are useless, because the free amino group of the peptide formed will react further with excess N-carboxyanhydride. Such N-carboxyanhydrides have therefore only been useful in peptide synthesis in solution, and even then mostly in aqueous solution, in which the intermediately formed peptide carbamate can be stabilized by strict adherence to certain conditions of pH and temperature for the short duration of the condensation reaction.

In an attempt to circumvent the abovementioned problems attending the otherwise attractive use of N-carboxyanhydrides, Block and Cox, cf. "Peptides, Proc. 5th Europ. Symp., Oxford September 1962", Pergamon Press 1963, Ed. G. T. Young, pp. 84–87, tried to prepare N-trityl-N-carboxyanhydrides of α-amino acids, but were only able to synthesize these derivatives of the simplest α-amino acids, viz. glycine and alanine. The same workers tried to prepare N-substituted N-carboxyanhydrides in which the N-substituent was benzyloxycarbonyl and tert.butoxycarbonyl, but reported that such derivatives could not be made. Apart from the fact that it was impossible to prepare the N-trityl derivatives of the N-carboxyanhydrides of other than the two simplest α-amino acids, it is common knowledge that N-trityl amino acids in various condensation methods of peptide synthesis produce low yields in the stepwise method of chain elongation, due to the considerable sterical hindrance imposed by the trityl group upon the carboxyl group of the attached amino acid. Thus, notwithstanding the results published in 1963 and the suggestion by Hanson and Law in 1965, cf. J. Chem. Soc. 1965, pp. 7284–7297, to use various methoxy-substituted benzhydryl groups as N-protecting groups for N-carboxyanhydrides, the work of recent years has mainly been directed at the use of unsubstituted N-carboxyanhydrides under closely controlled conditions, cf. e.g. Hirschmann et al. "The Controlled Synthesis of Peptides in Aqueous Medium. VIII. The Preparation and Use of Novel α-Amino Acid N-Carboxyanhydrides", J. Amer. Chem. Soc. 93:11, June 1971, pp. 2746–2754.

Considering the attractive aspects involved, the reason for the lack of progress in the known art development of N-carboxyanhydrides of α-amino acids carrying an N-substituent, which after the participation of the N-carboxyanhydride in the condensation reaction serves to protect the amino group of the resulting peptide against further reaction, may presumably be attributed to the fact that such N-substituted N-carboxyanhydrides must meet every condition in a very critical combination of conditions, namely:

(1) The N-substituted N-carboxyanhydrides in question should be reasonably easy to prepare,
(2) they should be stable, so as not to require special precautions in their storage,
(3) the derivatives should crystallize well, so as to facilitate isolation and characterization,
(4) the sterical hindrance exerted by the N-substituent upon the carboxyl group of the attached amino acid should be very small, in order that the condensation reaction may be complete within a reasonable time,
(5) the substituent in question should effectively protect the terminal amino group of the peptide prepared by the action of the N-carboxyanhydride, but on the other hand it should
(6) be easily removable from the peptide under conditions not conducive to damage even to sensitive peptide bonds, when the terminal amino group is to be made available for further reaction.

SUMMARY OF THE INVENTION

The present invention provides N-substituted N-carboxyanhydrides which meet the set of conditions formulated above, and which therefore open very wide perspectives for the future utilization of N-carboxyanhydrides in peptide synthesis.

The compounds of the invention are compounds of the formula I

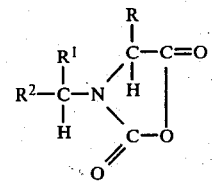

wherein R designates hydrogen or the side-chain of an α-amino acid, any functional group or functional groups in said side-chain being optionally protected, $R_1$ designates hydrogen, and $R_2$ designates phenyl pentasubstituted with lower alkoxy, or $R_1$ and $R_2$ together with the adjacent carbon atom designates a 9-xanthyl-, 9-thioxanthyl- or 9-selenoxanthyl group, said group being optionally substituted in positions othter than 1 and 8 with preferably lower alkyl, lower alkoxy, nitro, or chloro.

R in the above formula I designates the side-chain of any α-amino acid, and as examples of the most important amino acids used i peptide syntheses, the side-chains of which amino acids are comprised by the definition of R, may be mentioned alanine, arginine, aspartic acid, asparagine, cystine, cysteine, glutamic acid, glutamine, glycine (in the case of glycine, R=H, which is mentioned specifically in the above definition of R), histidine, isoleucine, leucine, lysine, methionine, phenylalanine, serine, threonine, tryptophan, tyrosine, and valine. Most of these α-amino acids contain functional groups in their side-chains, and in the compounds of the invention, such functional groups may be protected with protecting groups of the types conventionally used in the peptide synthesis art. However, one of the advantages of the compounds of the invention is that protection of side-chain functional groups is not necessary to the extent required in reagents for use in the classical peptide synthesis using condensing agents.

DETAILED DESCRIPTION OF THE INVENTION

As examples of the abovementioned lower alkyl groups may be mentioned methyl and ethyl, preferably methyl, and as examples of the abovementioned lower alkoxy groups may be mentioned methoxy and ethoxy, preferably methoxy.

Examples of especially interesting compounds of the general formula I are:

(1) N-Pentamethoxybenzyl-N-carboxyanhydrides of α-amino acids having the formula Ia

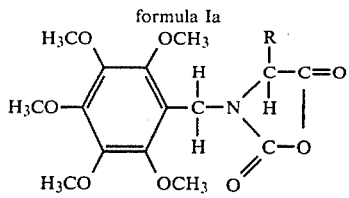

wherein R has the above meaning, and the corresponding pentaethoxybenzyl compounds, and (2) N-(9-xanthyl)-N-carboxyanhydrides of α-amino acids having the formula Ib

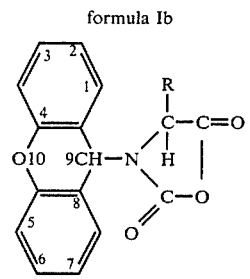

wherein R has the above meaning, and the corresponding 9-thioxanthyl and 9-selenoxanthyl compounds.

As examples of further especially interesting compounds of the formula I may be mentioned compounds of the formula I wherein the N-substituent

is one of the following:
  3,6-dimethoxy-9-xanthyl
  3,6-diethoxy-9-xanthyl
  3,6-dichloro-9-xanthyl
  3,6-dinitro-9-xanthyl
  2,7-dichloro-9-xanthyl
  2,7-dinitro-9-xanthyl
  4,5-dinitro-9-xanthyl
  4,5-dichloro-9-xanthyl
and the analogous 9-thioxanthyl and 9-selenoxanthyl compounds.

N-Substituted N-carboxyanhydrides of α-amino acids of the formula I are solid, well-crystallizing substances which may easily be prepared, isolated and characterized without special protective measures. Furthermore, they offer the obvious advantage of being stable on storage. Therefore, these compounds may be prepared in industrial scale and sold ready for use as peptide synthesis starting materials or reagents directly applicable as reactive amino acid derivatives without any pretreatment or any addition of activating reagent, but in spite of their reactivity in the peptide synthesis they can be handled and stored without risk of destruction. Due to the special N-substitution, the compounds according to the invention show the abovementioned typical advantages of the N-carboxyanhydrides with respect to suitable reactivity, freedom from formation of undesired rearrangement products and recovery of non-reacted excess, but, again due to the N-substitution, they are free from the disadvantages of the unsubstituted N-carboxyanhydrides, e.g. undesired further reaction between N-carboxyanhydride and the free amino group of the resulting peptide, disadvantages which hitherto limited the usefulness of N-carboxyanhydrides to syntheses in aqueous solution under carefully controlled conditions. Compared to the abovementioned known and previously suggested N-substituted N-carboxyanhydrides, the compounds according to the invention are superior in that they react faster and more completely with the N-terminal amino group which is to be acylated. Using the compounds according to the invention, peptide synthesis can be carried out according to the solution method or as a resin carrier method, and after the condensation, the N-substituent reappears as amino protecting group on the terminal nitrogen atom of the peptide, where it effectively protects this nitrogen atom against undesired further reaction with N-carboxyanhydride, but in spite of this, the special character of the group permits it to be easily removed by acid treatment in the subsequent deblocking step.

The present invention opens up the possibility of efficient and general use of N-carboxyanhydrides of α-amino acids in resin carrier syntheses, which means that the evident advantages of the resin carrier syntheses with respect to timesaving and automation can now be enjoyed with concomitant recovery of the reagent which must, in the resin carrier syntheses, necessarily be used in considerable excess. The recovery of non-reacted starting material in crystalline form is typically of the order of 50-80%.

The principle of a resin carrier synthesis, e.g. a solid-phase synthesis, using a compound of the formula I as starting material is illustrated schematically below:

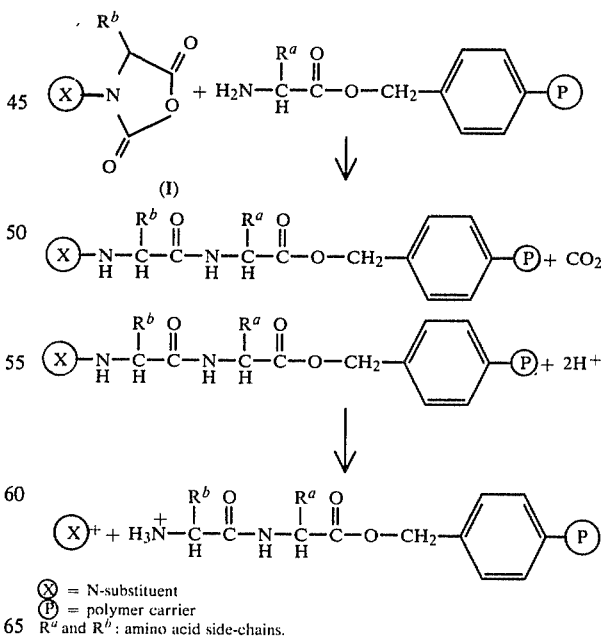

Ⓧ = N-substituent
Ⓟ = polymer carrier
$R^a$ and $R^b$: amino acid side-chains.

The above scheme shows that the N-substituent, X, reappears as amino protecting group in the resulting peptide and that it is removed by acid treatment subsequently to the condensation.

Among the N-substituents of the compounds of the formula I, 9-xanthyl has been suggested as amide protecting group for protecting the carboxamide function in asparagine and glutamine in peptide syntheses, cf. S. Akabori, S. Sakakibara and Y. Shimonishi, Bull. chem. Soc. Japan 34, 739 (1961), and Y. Shimonishi, S. Sakakibara, and S. Akabori, Bull. chem. Soc. Japan 35, 1966 (1962).

Asparagine and glutamine are amino acids, but they also contain a carboxamide function. In the classical synthesis of asparagine- and glutamine-containing peptides, the amide functions of which are not protected, numerous side-reactions have been noted, e.g. dehydration of these amide groups into nitrile groups, formation of isoasparagine or isoglutamine derivatives resulting from intermediate cyclic amides and cleavage of the amide function by acid or alkaline hydrolysis: By protecting these amide functions, e.g. as part of the above-mentioned "global" protection, such destructive side-reactions are avoided. The known use of the 9-xanthyl group for this purpose as amide protecting group for the carboxamide function in asparagine and glutamine does not anticipate the present invention, especially as the N-substituent of the N-carboxyanhydrides of the formula I is primarily an amino protecting group which exerts its protective effect on the amino group of the peptide formed by the reaction of the N-carboxyanhydride.

It is also known to prepare xanthyl derivatives of amides in order to characterize these amides in the organic chemical analysis, cf. Veibel, "The Identification of Organic Compounds", Gjellerup, Copenhagen.

The known art application of the 9-xanthyl group for protecting the amide groups in asparagine and glutamine and for derivatisation of amides for characterization, respectively, is remote from the invention of the N-substituted N-carboxyanhydrides of α-amino acids of the formula I showing excellent properties as intermediates in peptide syntheses.

The compounds of the formula I may e.g. be prepared in the following manner:

When $R_1$ in the desired end product is hydrogen, and $R_2$ is penta(lower alkoxy)phenyl, the starting material is a penta(lower alkoxy)benzaldehyde. The Schiff base of this aldehyde with the desired α-amino acid is prepared by treating the aldehyde with the α-amino acid dissolved in a base, e.g. aqueous sodium hydroxide, whereafter the Schiff base, which need not be isolated, is treated with a reducing agent such as sodium borohydride. By neutralization with acid, e.g. hydrochloric acid, to the isoelectric point of the N-substituted amino acid in question, said isoelectric point usually being in the pH range of 6-7, the substituted amino acid of the formula II

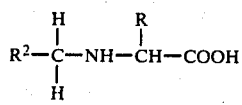

wherein R and $R_2$ are as defined above, precipitates, being less soluble than the corresponding free amino acids. This compound of the formula II may thereafter be converted into the corresponding N-carboxyanhydride in the manner described further below.

The starting material, penta(lower alkoxy)benzaldehyde, is prepared by known methods or analogously to known methods. Thus, pentamethoxybenzaldehyde is easily prepared in large scale from the commercially available and inexpensive 3,4,5-trimethoxybenzoic acid by the following series of reactions: bromination, replacement of the bromine atoms by methoxy groups through sodium methanolate, decarboxylation by destillation, and finally formylation by phosphorus oxychloride/N-methyl formanilide. (F. Dallacker, "Darstellung der Pentamethoxybenzoesäure", Liebigs Ann. Chem. 665 (1963) 78–83).

When $R_1$ and $R_2$ in the desired compound of the formula I together with the adjacent carbon atom form an optionally substituted 9-xanthyl, 9-thioxanthyl, or 9-selenoxanthyl group (which group is preferably a group of the formula A

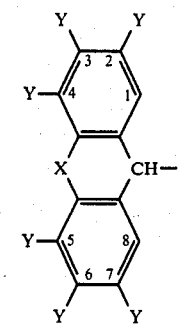

wherein X represents an oxygen, sulphur, or selenium atom, and the substituents Y are the same or different and each represents lower alkyl, lower alkoxy, nitro, or chloro, with the proviso that at least two of the symbols Y represent hydrogen), an ester of the desired amino acid, usually the methyl ester in the form of the hydrochloride, is reacted with an equivalent amount of the halide correponding to the desired N-substituent, usually the chloride, or of the alcohol corresponding to the desired N-substituent, usually by boiling the reaction components in a solvent such as chloroform in the presence of a base such as one equivalent of triethylamine or sodium bicarbonate and a drying agent such as magnesium sulfate. The reaction time is usually from a few hours to several days. When the boiling is finished, the reaction mixture is usually washed with water, whereafter the solvent is evaporated. The residue is usually an oil which maybe saponified directly, e.g. in solution in methanol using an excess of aqueous sodium hydroxide solution. Thereafter, the saponification solution may be concentrated, and the residue may be diluted with water, whereafter the resulting substituted amino acid may be precipitated by neutralization to the isoelectric point as described above. The resulting N-substituted amino acid has the formula III

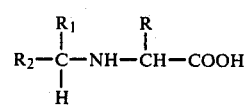

wherein R is as defined above, and $R_1$ and $R_2$ together with the adjacent carbon atom form an optionally substituted 9-xanthyl, 9-thioxanthyl, or 9-selenoxanthyl group, preferably a group of the formula A shown above.

The compounds of the above formula III are believed to be novel compounds, and these novel compounds are most interesting because of the remarkable lability of the N-substituent, which makes these compounds useful and valuable as N-protected amino acid derivatives usable as starting compounds or intermediates in peptide syntheses, and hence, one aspect of the present invention relates to the novel compounds of the formula III.

The further conversion of the compounds of the formulae II and III to form the N-substituted N-carboxyanhydrides of α-amino acids of the formula I may be performed e.g. by bubbling phosgene through a solution of the compound II or III or an alkali metal salt thereof in a solvent such as tetrahydrofuran. It is also possible to add a solution of an alkali metal salt of a compound with the formula II or III in a solvent such as tetrahydrofuran dropwise to a solution of phosgene, suitably in the same solvent. Alkali metal salts of the amino acids of the formula II or III may be prepared e.g. by dissolving the amino acid in an aquimolar amount of 1 N sodium hydroxide or other alkalimetal hydroxide, filtering the solution and freeze-drying the filtrate. The resulting products of the formula I may be worked up by concentration of the reaction solution in vacuum, fractionated precipitation of the residue and purification of the N-carboxyanhydride-containing fraction by passing through a column of silicagel using e.g. chloroform as eluent. By concentration of the eluate, and if necessary, seeding, the desired compound of the formula I crystallizes.

The abovementioned halides used as starting materials for the preparation of compounds of the formula III may e.g. be prepared from the corresponding alcohols (which are also usable per se as starting materials), the alcohols being obtainable e.g. from the corresponding ketones.

The xanthones, thioxanthones and selenoxanthones used as starting materials, are, with the exception of the commercially available parent compounds xanthone and thioxanthone, made from the appropriately substituted diphenylether 2-carboxylic acids, which, in their turn, are synthesized from commercially available and mostly inexpensive phenol - and benzoic acid derivatives.

Thus, e.g. 4-chloro-thiophenol and 2-iodo-benzoic acid are condensed to give 2-carboxy-4'-chlorodiphenylsulfide, which is then cyclized to 2-chloro-thioxanthone (cf. J. O. Jilek, M. Rajsner, J. Pomykacek and M. Protiva, Cesk. Farm. 14, (1965) 294–303). In an analogous manner, 4,5-dichlorothioxanthone is obtained from 2-(o-chlorophenylthio)-3-chlorobenzoic acid (cf. V. G. Kalawar, V. V. Badiger and K. S. Nargund, J. Karnatak Univ. 11, (1966) 37–41). Selenoxanthone is obtained from 2-(phenylseleno)-benzoic acid, made by the condensation of selenophenol with 2-iodobenzoic acid; 2-chloro-selenoxanthone is synthesized from 2-(p-chlorophenylseleno)-benzoic acid, obtained from 4-chloroselenophenol and 2-iodobenzoic acid (cf. K. Sindelar, E. Svatek, J. Metysova, J. Metys and M. Protiva, Collection Czechoslovak Chem. Commun. 34, (1969) 3792–3800). 3-Methoxy xanthone is analogously obtained from 2-carboxy-3'-methoxy diphenyl ether, 3-chloro-6-methoxy-xanthone from 2-carboxy,5-chloro-3'-methoxy diphenyl ether and 3-methyl-xanthone from 2-carboxy,5-methyl diphenyl ether. 3,6-Dimethoxy-xanthone is obtained from the abovementioned 3-chloro,6-methoxy-xanthone by the facile replacement of chloride with methoxy (cf. A. A. Goldberg and A. H. Wragg, J. Chem. Soc. 1958, 4227–4234 and ibid. 4234–4241). Similarly, 3-nitro-xanthone is obtained from 2-carboxy,5-nitrodiphenyl ether and 4-nitroxanthone from 2-carboxy,6-nitro diphenyl ether, whereas 2-nitroxanthone and 2,7-dinitro-xanthone may be obtained by direct nitration of xanthone (cf. A. A. Goldberg and H. A. Walker, J. Chem. Soc. 1953, 1348–1357).

The preparation of the xanthhydrols, thioxanthhydrols and selenoxanthhydrols is readily achieved by the reduction of the xanthones, thioxanthones, or selenoxanthones obtainable commercially or by synthesis as described above, e.g. by treatment of their boiling tetrahydrofuran or methanol solutions with an excess of sodium borohydride, concentration to dryness, and crystallization from e.g. acetone/petroleum ether (cf. e.g. C. C. Price, M. Hori, T. Parasaran, and M. Polk, J. Amer. Chem. Soc. 85, (1963) 2278–2282).

The conversion to the halides may be performed according to M. Gomberg and L. H. Cone, Liebigs Ann. Chem. 376, (1910) 183–238, simply by passing dry hydrogen chloride or hydrogen bromide gas through a solution of the pertinent xanthhydrol in a suitable, dry solvent, such as ether, in the presence of a drying agent, such as calcium chloride. Occasionally, however, a low chloride content (cf. Gomberg and Cone, p. 188) and the reappearance of ketone absorption in the infra-red range at 1650 cm$^{-1}$ may be observed (cf. also T. P. Hilditch and S. Smiles, J. Chem. Soc. 99, (1911) 145–160 and J. F. Muren, J. Med. Chem. 13, (1970) 140–141). The alternative preparation procedure makes direct use of the corresponding xanthhydrols, from which the halides are formed in situ by the action of the hydrohalide of the amino acid ester.

The invention also comprises an improved method for the preparation of N-xanthyl-α-amino acid N-carboxyanhydrides (Xth NCAs) by direct reaction of xanthhydrol with the NH group of unsubstituted α-amino-N-carboxyanhydrides (free NCAs).

Xanthhydrol is widely used in the derivation of primary amides R-CO-NH$_2$ for purposes of identification (Phillips and Pitt, J. Amer. Chem. J. 65 1355 (1943)). Furthermore, as mentioned on page 15, 9-xanthyl has been suggested for protecting the primary amide —CO—NH$_2$ group of asparagine and glutamine during peptide synthesis. For all of these derivatives, the known method of synthesis consists of treatment with xanthhydrol in acetic acid solution, the acetic acid functioning both as a catalyst and as solvent.

Due to the reactive nature of NCAs, acetic acid cannot be used in the preparation of Xth NCAs, since it will lead to an opening of the cyclic anhydride. Moreover, the presence of water, which is formed in the condensation reaction, cannot be tolerated, since it will cause extensive polymerization of the free NCA.

Aromatic hydrocarbons, on the other hand, while being unreactive, are good solvents for xanthhydrol and free NCAs. Further, what is most important, the use of refluxing benzene, toluene, xylene and other lower alkylbenzenes results in the instant removal of the water generated in the reaction, due to the lower boiling point of the azeotropic mixture. Being insoluble in the aromatic hydrocarbon, the water separates as droplets in the condensate. By the use of a water separator, the water is trapped, while the aromatic hydrocarbon flows back into the reaction mixture. In this manner, the water is removed as soon as it is formed, and losses due to the polymerization of the free NCA are reduced considerably.

Reaction Scheme

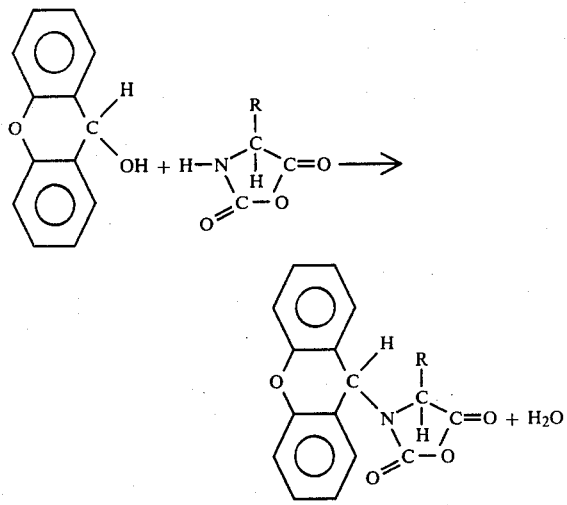

Moreover, the appearance of water in the condensate provides visual control of the rate and extent of the reaction.

The starting materials, i.e. the free NCAs (protected, if required, on side chain functional groups), are easily prepared from the corresponding α-amino acids in high yields by the method of Fuller, Verlander and Goodman, Biopolymers 15 1869 (1976).

The direct condensation of xanthhydrol with free NCA may also be performed with chemical trapping of the generated water. Thus, brief boiling of the reactants, dissolved in e.g. acetic anhydride, also affords the Xth NCAs in good yield, the water being instantly consumed by the acetic anhydride to form acetic acid. In many cases, this embodiment seems to give better yields than the use of a water separator.

Thus, the direct condensation of xanthhydrol with free NCA under conditions in which the water generated in the condensation is removed, constitutes a preferred embodiment of the present invention.

The invention also relates to a process for preparing peptides by coupling the N-terminal amino group of amino acids or peptides with reactive amino acid derivatives using N-substituted N-carboxyanhydrides of α-amino acids of the formula I as reactive amino acid derivatives.

This process may be performed in solution or as a resin carrier synthesis. Because of the considerable advantages of the resin carrier syntheses with respect to timesaving and the possibility of automation, the process is preferably carried out as a resin carrier synthesis.

When the peptide synthesis using the compounds of the formula I is carried out in solution, substantially equimolar amounts of amino component and acid component of the formula I are used, like in the classical peptide synthesis, but needless to say, no activating reagents such as diimides are used. The peptide synthesis according to the solid-phase principle using the compounds of the formula I is distinguished from the solution principle primarily by using the abovementioned excess of reagent and washing-out of non-reacted excess reagent, and such a peptide synthesis comprises essentially the following operations per cycle: Addition of reagent of the formula I, reaction time during which the coupling takes place, washing-out of excess reagent, deblocking, usually with trifluoroacetic acid, washing-out of excess trifluoroacetic acid and neutralization with e.g. triethylamine. After the neutralization stage, the next synthesis stage may be performed using a corresponding sequence with a different or the same reagent of the formula I.

On certain very special amino acids such as proline no N-substituted N-carboxyanhydrides may be prepared; in the case of proline, this is because proline is not a proper α-amino acid, but rather a cyclized α-imino acid, which, because of the cyclization, is not able to form a N-substituted N-carboxyanhydride with retention of its identity. In the case of such amino acids, the peptide synthesis must be performed using a derivative suitable for the amino acid in question and possibly a suitable activating reagent to obtain incorporation of the amino acid. For example, the special amino acid, N-protected with a tert.butyloxycarbonyl group, can be used together with N,N'-dicyclohexylcarbodiimide.

In the peptide synthesis, the removal of the N-substituent introduced using compounds of the formula I, said N-substituent functioning as a protecting group for the N-terminus of the peptide, may be performed by acid treatment under mild and acceptable conditions because of the special character of the substituent.

Thus, e.g. the pentamethoxybenzyl group is removed from N-pentamethoxybenzyl peptides by treatment for one hour at room temperature with anhydrous trifluoracetic acid in the presence of resorcinol dimethyl ether or anisole. The N-xanthyl, N-thioxanthyl, and N-selenoxanthyl groups may be removed under extremely mild acidic conditions, such as exposure to a 5% solution of trifluoracetic acid in e.g. methylene chloride or dry ether. Moreoever, they are susceptible to acid-catalyzed methanolysis in e.g. a solution of methanol and acetic acid in chloroform.

In resin carrier syntheses using compounds of the formula I, the recovery of excess starting compound may be performed by concentrating the separated solution containing excess reagent on a rotatory evaporator, whereby the compound of the formula I either crystallizes during the evaporation or during subsequent drying in vacuum, if necesssary by seeding.

Experience has shown that in peptide syntheses, valine is one of the most difficultly introduceable amino acids because of its structure, and especially the sequence valyl-phenylalanine often involves problems. Therefore, it is especially interesting to note that within the scope of the present invention, valine derivatives of the formula I have been prepared and have been found to react satisfactorily in peptide syntheses, especially also in connection with the establishment of the sequence valylphenylalanine. On this basis it may be concluded that the compounds of the formula I are quite generally preparable and applicable.

The invention is further illustrated through the following examples, all amino acids used in the examples being L-amino acids.

EXAMPLE 1

N-Pentamethoxybenzyl-leucine (PMB-Leu)

13 g of leucine is dissolved in 50 ml of 2 N sodium hydroxide solution, and 15 g of pentamethoxybenzaldehyde is added in small portions with vigorous stirring. After 20 minutes, 1.2 g of sodium borohydride is added in small portions, also with vigorous stirring. 20 minutes later, the procedure of adding aldehyde and sodium borohydride is repeated. 30 minutes after the last addition, the solution is brought to pH 6-7 by careful addition of 4 N hydrochloric acid, leading to precipitation of the product. It is isolated by filtration, washed thoroughly with water and petroleum ether, and dried in vacuo. The yield of nearly white product is 20 g.

EXAMPLE 2

N-Pentamethoxybenzyl-alanine (PMB-Ala)

This compound is prepared as described in example 1 but using alanine instead of leucine.

EXAMPLE 3

N-Pentamethoxybenzyl-valine (PMB-Val)

This compound is prepared as described in example 1 but using valine instead of leucine.

EXAMPLE 4

N-Pentamethoxybenzyl-glycine (PMB-Gly)

This compound is prepared as described in example 1 but using glycine instead of leucine.

EXAMPLE 5

N-Pentamethoxybenzyl-phenylalanine (PMB-Phe)

This compound is also synthesized as specified in example 1, but using phenylalanine instead of leucine.

EXAMPLE 6

N-(Thioxanthyl)-leucine methyl ester (Sxt-Leu-OMe)

22 g of thioxanthhydrol together with 20 g of calcium chloride is suspended in 150 ml of dry ether, and after expulsion of the air in the apparatus by dry nitrogen dry hydrogen chloride is passed through the mixture, external cooling being applied, to keep the temperature below 10°-15° C. After 15-30 minutes, the mixture is filtered, the filtrate is concentrated to dryness on the rotatory evaporator, and the residue dried to 0.1 mm Hg. The product, together with 18 g of leucine methyl ester hydrochloride, is dissolved in 200 ml of chloroform by warming, and the solution, after addition of 30 ml of triethylamine, is refluxed for 48 hours. The solution is allowed to cool, and is washed twice with water, dried over magnesium sulfate, and concentrated to dryness. The residue crystallizes upon drying i vacuo.

EXAMPLE 7

N-(4-Nitroxanthyl)-leucine methyl ester (Xth($NO_2$)-Leu-OMe)

This compound is prepared as described in example 6, but using 4-nitroxanthhydrol instead of thioxanthhydrol.

EXAMPLE 8

N-(2-Chloro-thioxanthyl)-valine methyl ester (Sxt(Cl)-Val-OMe)

This compound is prepared as described in example 6 but using valine methyl ester hydrochloride instead of leucine methyl ester hydrochloride, hydrogen bromide instead of hydrogenchloride in dry benzene instead of dry ether, and 2-chlorothioxanthhydrol instead of thioxanthhydrol.

EXAMPLE 9

N-(Thioxanthyl)-leucine (Sxt-Leu)

20 g of the methyl ester obtained above is saponified in 150 ml of methanol by addition of 16 ml of 6 N sodium hydroxide, and heating the solution under reflux for 2 hours. The cooled solution is concentrated to dryness on a rotatory evaporator, and the residue is dissolved in 150 ml of water. The solution is carefully neutralized by dropwise addition of hydrochloric acid, upon which the product precipitates. It is isolated by filtration, and washed copiously with water and petroleum ether, and dried.

EXAMPLE 10

N-(Xanthyl)-valine methyl ester (Xth-Val-OMe)

A mixture of 20 g of valine methyl ester hydrochloride, 20 g of crystalline xanthhydrol, 20 g of sodium bicarbonate and 20 g of anhydrous magnesium sulfate is suspended in 400 ml of chloroform, and the mixture heated to reflux for 24 hours, after which time it is filtered. The filtrate upon concentration on a rotatory evaporator leaves an oily residue, which crystallizes during drying in vacuo. After recrystallization from hot methanol, 20 g of product is obtained, of m.p. 85°-87° C., slightly contaminated with xanthone. It is used without further purification as specified below.

EXAMPLE 11

N-(Xanthyl)-leucine methyl ester (Xth-Leu-OMe)

This compound is prepared as described in example 10, but using leucine methyl ester hydrochloride instead of valine methyl ester hydrochloride.

EXAMPLE 12

N-(Xanthyl)-phenylalanine methyl ester (Xth-Phe-OMe)

This compound is prepared as described in example 10, but using phenylalanine methyl ester hydrochloride instead of valine methyl ester hydrochloride.

EXAMPLE 13

N-(Xanthyl)-tryptophan methyl ester (Xth-Trp-OMe)

This compound is prepared as described in example 10, but using tryptophan methyl ester hydrochloride instead of valine methyl ester hydrochloride.

EXAMPLE 14

N-(Xanthyl)-valine (Xth-Val)

16 g of the methyl ester obtained above is saponified by 15 ml of 6 N sodium hydroxide in 125 ml of methanol, boiling for 4 hours under reflux. The solution in concentrated to dryness, and the residue is dissolved in 150 ml of water. Undissolved material (3 g) is removed by filtration, and the clear, yellowish solution is carefully brought to pH 7-8 by dropwise addition of hydrochloric acid. The precipitated product is isolated by filtration, and washed well with petroleum ether. The yield is 9 g, m.p. 186°-189° C. (dec.).

EXAMPLE 15

N-(Xanthyl)-tryptophan (Xth-Trp)

This compound is prepared as described in example 14, but using xanthyl-tryptophan methyl ester instead of xanthylvaline methyl ester and saponifying for one and a half hours instead of 4 hours. M.p. 215°–220° (dec.)

EXAMPLE 16

N-Carboxyanhydride of N-(xanthyl)-valine (Xth-Val NCA)

6 g of Xth-Val is dissolved in 50 ml of tetrahydrofuran by warming, and phosgene is passed through the solution for 30 minutes while it is boiling under reflux, externally stirred with the aid of a teflon-coated magnetic stirring bar. After concentration of the solution to dryness, reprecipitation of the residue and passage through a column of silicagel, the product crystallizes directly from ether/petroleum ether. The yield is 2 g of white, crystalline Xth-Val NCA of m.p. 105°–106°, $[\alpha]_{578}^{20} = +73.1°$ (c=1, benzene).

Alternatively, the sodium- or alkali metal salt of Xth-Val is treated with phosgene as described above. For the preparation of the salt, Xth-Val is dissolved in an equivalent quantity of e.g. N sodium hydroxide or other alkali hydroxide solution, whereupon the solution is filtered and freeze-dried.

EXAMPLE 17

N-Carboxyanhydride of N-(thioxanthyl)-leucine (Sxt-Leu NCA)

This compound is prepared as described in example 16 but using Sxt-Leu instead of Xth-Val.

Example 18

N-Carboxyanhydride of N-(xanthyl)-phenylalanine (Xth-Phe NCA)

This compound is prepared as described in example 16, but using Xth-Phe instead of Xth-Val.

EXAMPLE 19

N-Carboxyanhydride of N-pentamethoxybenzyl-alanine (PMB-Ala NCA)

This compound is prepared as described in example 16, but using PMB-Ala instead of Xth-Val.

EXAMPLE 20

Synthesis of a dipeptide, Xth-Val-Phe-OMe, by synthesis in solution 0.5 g oily phenylalanine methyl ester is dissolved in 10 ml of benzene. After addition of 1.6 g crystalline Xth-Val NCA, the clear solution is kept for 5 hours at 30° C., after which it is concentrated to dryness in vacuo. The oily residue slowly crystallizes upon drying in high vacuum. Recrystallized from 5 ml benzene/25 ml petroleum ether, the product is obtained in 80% yield as colourless needles, m.p. 122°–123° C., $[\alpha]_{578}^{20} - 32.7°$ (c=1, benzene).

Analysis: Calculated for $C_{28}H_{30}N_2O_4$ (458.6): %C 73.3; %H 6.6; %N 6.1; %O 14.0. Found: %C 73.4; %H 6.4; %N 5.9; %O 14.1.

EXAMPLE 21

Synthesis of the same dipeptide, Xth-Val-Phe-OMe, by resin carrier synthesis 1 g of phenylalanyl-resin (0.5 mmol Phe per g), obtained by esterifying tert.butoxycarbonyl-phenylalanine to chloromethylated Bio-Beads SX-2, followed by liberation of the amino groups, is stirred for 24 hours in 12 ml of benzene, containing 1 g of crystalline Xth-Val NCA, at 30° C. After filtration, the peptide-resin is washed thoroughly with benzene, and is then stirred for 24 hours in 25 ml of N methanolic triethylamine at 30° C. Evaporation of the filtrate leaves an oil, which is crystallized as described above to give 85% yield of Xth-Val-Phe-OMe, identical with the product obtained above.

EXAMPLE 22

Synthesis of a dipeptide, Xth-Val-Ala-OMe, in solution

This compound is prepared as described in example 20, but using alanine methyl ester instead of phenylalanine methyl ester. M.p. 81°–84° C., $[\alpha]_{578}^{20} = -39,0°$ (c=1, benzene).

EXAMPLE 23

Synthesis of a dipeptide, Sxt-Leu-Ala-OMe, in solution

This compound is prepared as described in example 20, but using Sxt-Leu NCA instead of Xth-Val NCA.

EXAMPLE 24

Synthesis of a dipetide, Xth-Phe-Ala-OMe, in solution

This compound is prepared as described in example 20, but using Xth-Phe-NCA instead of Xth-Val NCA.

EXAMPLE 25

Synthesis of a dipeptide, PMB-Ala-Pro-OMe, in solution

This compound is prepared as described in example 20, but using PMB-Ala NCA instead of Xth-Val NCA and using proline methyl ester instead of alanine methyl ester.

EXAMPLE 26

N-Carboxyanhydride of N,S-dixanthyl-cysteine (Xth-Cys(Xth) NCA)

9 g of the N-carboxyanhydride of S-xanthyl-cysteine and 18 g of xanthhydrol is heated to reflux in 200 ml of toluene, externally stirred with the aid of a teflon-coated magnetic stirring bar. The reflux condensor is connected to a water-separator, and during the next 20–30 minutes a total of 0.4 ml of water is collected. The solution is cooled to ca. −10°, allowing unreacted xanthhydrol and polymeric impurities to be removed by filtration. The filtrate is concentrated under reduced pressure, and the residue crystallized from ethyl acetate by addition of petroleum ether. The yield of colourless crystals of m.p. 145°–146° is 9 g (64%). $[\alpha]_{578}^{20} = +272.1°$ (c=1 in benzene).

EXAMPLE 27

N-Carboxyanhydride of N-xanthyl-valine (Xth-Val NCA)

This compound is prepared as described in example 26, but using the N-carboxyanhydride of valine. Yield: 58%, m.p. 115°–116°, $[\alpha]_{578}^{20} = +81.5°$ (c=1 in benzene).

EXAMPLE 28

N-Carboxyanhydride of N-xanthyl, O-acetyl-tyrosine (Xth-Tyr(Ac) NCA)

This compound is prepared as described in example 26, but using the N-carboxyanhydride of O-acetyl-tyrosine. Yield: 70%,, m.p. 113°–114°, $[\alpha]_{578}^{20} = +56.6°$ (c=1 in benzene).

EXAMPLE 29

N-Carboxyanhydride of N-xanthyl-alanine (Xth-Ala NCA)

This compound is prepared as described in example 26, but using the N-carboxyanhydride of alanine. Yield: 50%, m.p. 118°–119°, $[\alpha]_{578}^{20} = +64.0°$ (c=1 in benzene).

EXAMPLE 30

N-Carboxyanhydride of N-xanthyl-isoleucine (Xth-Ilc NCA)

This compound is prepared as described in example 26, but using the N-carboxyanhydride of isoleucine. Yield: 35%, m.p. 172°–173°, $[\alpha]_{578}^{20} = +71.3°$ (c=1 in benzene).

EXAMPLE 31

N-Carboxyanhydride of N-xanthyl-glutamic acid γ-methyl ester (Xth-Glu(OMe) NCA)

This compound is prepared as described in example 26, but using the N-carboxyanhydride of glutamic acid γ-methyl ester. Yield: 36%, m.p. 99°–100°, $[\alpha]_{578}^{20} = +82.3°$ (c=1 in benzene).

EXAMPLE 32

N-Carboxyanhydride of N-xanthyl-leucine (Xth-Leu NCA)

This compound is prepared as described in example 26, but using the N-carboxyanhydride of leucine. Yield: 56%, m.p. 131°, $[\alpha]_{578}^{20} = +60.2°$ (c=1 in benzene).

EXAMPLE 33

N-Carboxyanhydride of N-xanthyl-glutamic acid γ-methyl ester (Xth-Glu(OMe) NCA)

3.5 g of the N-carboxyanhydride of glutamic acid γ-methyl ester and 10 g of xanthhydrol is boiled under reflux for 10 minutes in 150 ml of acetic anhydride. After cooling to room temperature, the mixture is filtered, and the filtrate concentrated to dryness in vacuo. The oily residue is reprecipitated from ethyl acetate by addition of petroleum ether. The oily product crystallizes on standing at room temperature, and is recrystallized from ethyl acetate/petroleum ether. The yield of colourless crystals of m.p. 100° is 4.0 g (58%). $[\alpha]_{578}^{20} = +86.7°$ (c=1 in benzene).

We claim:

1. N-substituted N-carboxyanhydrides of α-amino acids, having the general formula I

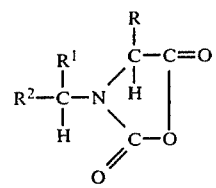

wherein R designates hydrogen or the side-chain of an α-amino acid, any functional group or functional groups in said side-chain being optionally protected, $R_1$ and $R_2$ together with the adjacent carbon atom designates $R_9$-xanthyl-, $R_9$-thioxanthyl- or 9-selenoxanthyl group, said group being optionally substituted in positions other than 1 and 8 with probably lower alkyl, lower alkoxy, nitro, or chloro.

2. N-substituted N-carboxyanhydrides of α-amino acids as claimed in claim 1, having the general formula

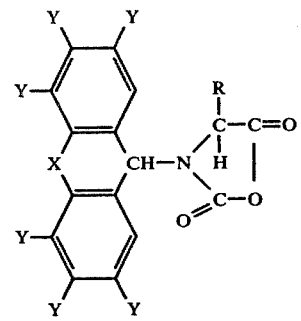

wherein R is as defined in claim 1, X designates an oxygen, sulfur, or selenium atom, and the substituents Y are the same or different and each designate hydrogen, lower alkyl, lower alkoxy, nitro, or chloro, with the proviso that at least two of the symbols Y designate hydrogen.

3. N-substituted N-carboxyanhydrides of α-amino acids as claimed in claim 2, wherein X is oxygen, and each symbol Y designates hydrogen.

4. N-substituted N-carboxyanhydrides as claimed in claim 2, wherein X is sulfur, and each symbol Y designates hydrogen.

5. N-substituted N-carboxyanhydrides as claimed in claim 2, wherein X is selenium, and each symbol Y designates hydrogen.

* * * * *

UNITED STATES PATENT AND TRADEMARK OFFICE
CERTIFICATE OF CORRECTION

PATENT NO. : 4,267,344
DATED : May 12, 1981
INVENTOR(S) : JOHN B. HALSTROM, et al

It is certified that error appears in the above—identified patent and that said Letters Patent is hereby corrected as shown below:

Column 1, line 58: "fr" should read --or--.

Column 2, line 14: "less" should read --loss--.

Column 19, line 11: "(Xth-Ilc" should read --(Xth-Ile--.

Signed and Sealed this

Twenty-seventh Day of October 1981

[SEAL]

Attest:

GERALD J. MOSSINGHOFF

Attesting Officer    Commissioner of Patents and Trademarks